(12) United States Patent
Cedro, Jr. et al.

(10) Patent No.: US 11,832,825 B2
(45) Date of Patent: Dec. 5, 2023

(54) METHODS AND DEVICES FOR CONTROLLING THE SIZE OF EMPHYSEMATOUS BULLAE

(71) Applicant: Ethicon, Inc., Somerville, NJ (US)

(72) Inventors: Rudolph Cedro, Jr., Clinton, NJ (US); Kevin S. Weadock, Hillsborough, NJ (US); Leo B. Kriksunov, Ithaca, NY (US)

(73) Assignee: Ethicon, Inc., Raritan, NJ (US)

( * ) Notice: Subject to any disclaimer, the term of this patent is extended or adjusted under 35 U.S.C. 154(b) by 988 days.

(21) Appl. No.: 16/672,701

(22) Filed: Nov. 4, 2019

(65) Prior Publication Data

US 2020/0078023 A1    Mar. 12, 2020

Related U.S. Application Data

(62) Division of application No. 14/795,172, filed on Jul. 9, 2015, now abandoned.

(Continued)

(51) Int. Cl.
*A61B 17/12* (2006.01)
*A61B 17/128* (2006.01)

(Continued)

(52) U.S. Cl.
CPC ...... *A61B 17/12104* (2013.01); *A61B 17/064* (2013.01); *A61B 17/1227* (2013.01); *A61B 17/12036* (2013.01); *A61B 17/1285* (2013.01); *A61B 17/12131* (2013.01); *A61B 17/12172* (2013.01); *A61B 17/1204* (2013.01); *A61B 2017/00477* (2013.01); *A61B 2017/00862* (2013.01); *A61B 2017/00867* (2013.01); *A61B 2017/00876* (2013.01);

(Continued)

(58) Field of Classification Search
CPC ........ A61B 17/12104; A61B 17/12172; A61B 17/1227; A61B 17/12131; A61B 17/1204; A61B 2017/00986; A61B 2017/12086; A61B 2017/0645; A61B 2017/242; A61B 2017/12054

See application file for complete search history.

(56) References Cited

U.S. PATENT DOCUMENTS 5,507,754 A   4/1996  Green et al.
6,080,182 A   6/2000  Shaw et al.

(Continued)

FOREIGN PATENT DOCUMENTS

JP   2012-527317      11/2012
WO   WO 2001/066190    9/2001

(Continued)

OTHER PUBLICATIONS

Gompelmann D., et al. 'Predicting Atelectasis by Assessment of Collateral Ventilation prior to Endobronchial Lung Volume Reduction: A Feasibility Study.' Respiration. (2010) 80(5) pp. 419-425.

(Continued)

*Primary Examiner* — Anh T Dang

(57) ABSTRACT

An implantable device for control over the size of emphysematous bullae in a lung, including: an elongated central region having a fixed axial length; a first end including a first anchor; and a second end including a second anchor.

19 Claims, 6 Drawing Sheets

Related U.S. Application Data

(60) Provisional application No. 62/026,174, filed on Jul. 18, 2014.

(51) Int. Cl.
*A61B 17/122* (2006.01)
*A61B 17/064* (2006.01)
*A61B 17/00* (2006.01)
*A61B 17/24* (2006.01)

(52) U.S. Cl.
CPC .............. *A61B 2017/00986* (2013.01); *A61B 2017/0641* (2013.01); *A61B 2017/0645* (2013.01); *A61B 2017/12054* (2013.01); *A61B 2017/12086* (2013.01); *A61B 2017/242* (2013.01)

(56) References Cited

U.S. PATENT DOCUMENTS

| | | | |
|---|---|---|---|
| 6,174,323 | B1 | 1/2001 | Biggs et al. |
| 6,514,290 | B1 | 2/2003 | Loomas |
| 6,599,311 | B1 | 7/2003 | Biggs et al. |
| 6,997,189 | B2 | 2/2006 | Biggs et al. |
| 7,434,578 | B2 | 10/2008 | Dillard et al. |
| 7,757,692 | B2 | 7/2010 | Alferness et al. |
| 8,142,455 | B2 | 3/2012 | Thompson et al. |
| 8,157,823 | B2 | 4/2012 | Aronson et al. |
| 8,157,837 | B2 | 4/2012 | Thompson et al. |
| 8,186,355 | B2 | 5/2012 | Vander Burg et al. |
| 8,282,660 | B2 | 10/2012 | Thompson et al. |
| 8,323,202 | B2 | 12/2012 | Roschak et al. |
| 8,632,605 | B2 | 1/2014 | Thompson et al. |
| 2004/0078054 | A1 | 4/2004 | Biggs et al. |
| 2004/0143282 | A1 | 7/2004 | Dillard et al. |
| 2007/0073337 | A1 | 3/2007 | Abbott et al. |
| 2008/0215072 | A1 | 9/2008 | Kelly |
| 2010/0305715 | A1 | 12/2010 | Mathis et al. |
| 2013/0096603 | A1* | 4/2013 | Mathis ................ A61M 16/208 606/191 |
| 2013/0184579 | A1 | 7/2013 | Roschak et al. |
| 2015/0051709 | A1* | 2/2015 | Vasquez ........... A61B 17/12036 623/23.65 |
| 2016/0015394 | A1 | 1/2016 | Cedro et al. |

FOREIGN PATENT DOCUMENTS

| | | |
|---|---|---|
| WO | WO 2013/003632 | 1/2013 |
| WO | WO 2013/028579 | 2/2013 |

OTHER PUBLICATIONS

Herth FJ, Eberhard R, Gompelmann D.Slebos DJ.Ernst A.. Bronchoscopic lung volume reduction with a dedicated coil: a clinical pilot study. Ther Adv Respir Dis. 2010;4(4):225-231.
Sciurba F.C. et al. 'A Randomized Study of Endobronchial Valves for Advanced Emphysema.' N Engl J Med. (2010) 363(13) pp. 1233-1244.
Wood D.E. et al. 'A multicenter trial of an intrabronchial valve for treatment of severe emphysema.' J Thorac Cardiovasc Surg. (2007) 133(1) pp. 65-73.
Australian Office Action, Examination Report No. 1 for standard patent application, dated Apr. 17, 2019 for Application No. 2015290043, 4 pages.
Australian Office Action, Examination Report No. 2 for standard patent application, dated Jun. 11, 2019 for Application No. 2015290043, 3 pages.
Chinese Office Action, The First Office Action, and Search Report dated Sep. 28, 2018 for Application No. 201580039193.4, 11 pages.
Chinese Office Action, The Second Office Action, dated Jun. 5, 2019 for Application No. 201580039193.4, 7 pages.
Chinese Office Action, The Third Office Action, dated Jan. 19, 2020 for Application No. 201580039193.4, 7 pages.
European Examination Report dated May 22, 2018 for Application No. 15745305.1, 5 pages.
International Search Report and Written Opinion dated Sep. 23, 2015 for International Application No. PCT/US2015/039705, 14 pages.
International Search Report and Written Opinion dated Oct. 27, 2015 for International Application No. PCT/US2015/039708, 15 pages.
Japanese Office Action, Notification of Reasons for Refusal dated Mar. 19, 2019 for Application No. 2017-502842, 4 pages.
U.S. Appl. No. 14/795,268, filed Jul. 9, 2015.

* cited by examiner

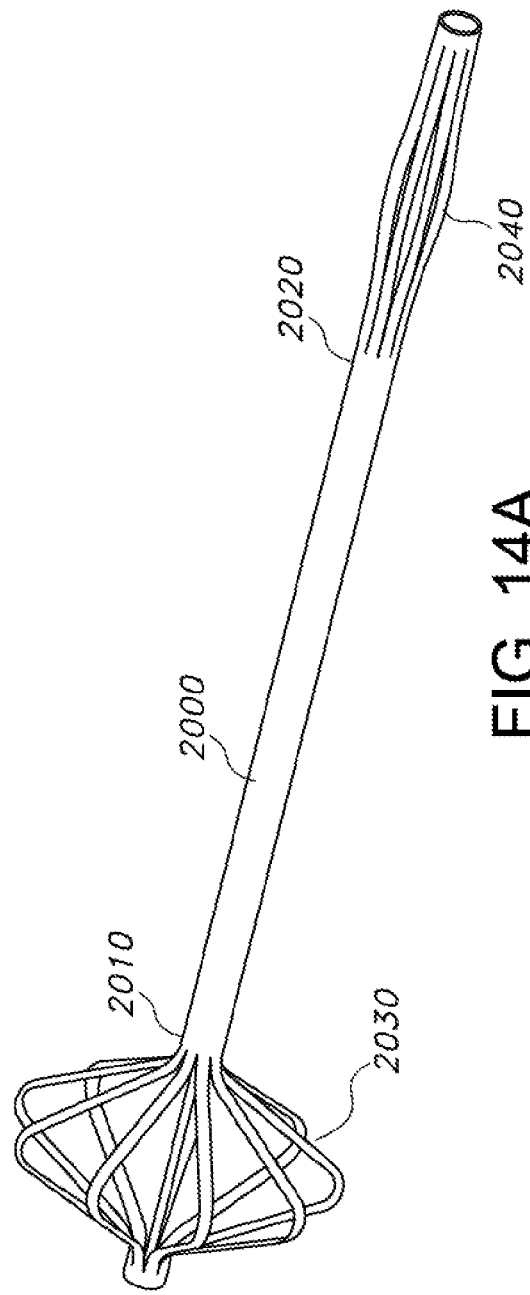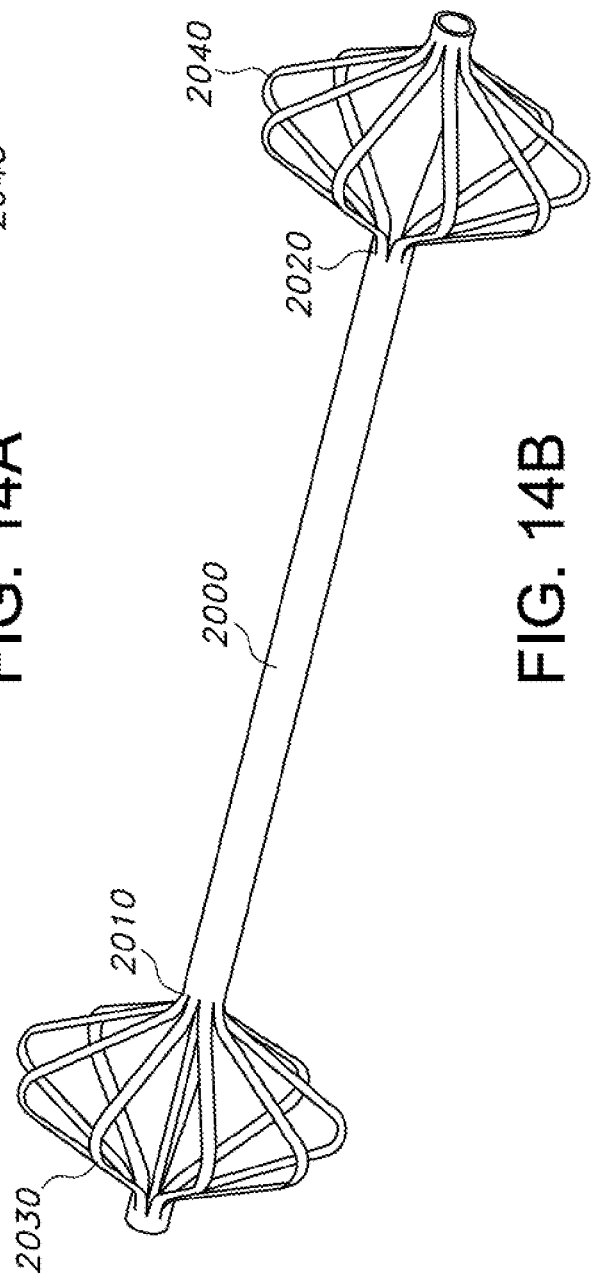
FIG. 14A
FIG. 14B

METHODS AND DEVICES FOR CONTROLLING THE SIZE OF EMPHYSEMATOUS BULLAE

CROSS REFERENCE TO RELATED APPLICATIONS

This application is a divisional of U.S. patent application Ser. No. 14/795,172, entitled "Methods and Devices for Controlling the Size of Emphysematous Bullae," filed Jul. 9, 2015, now abandoned, which claims the priority to U.S. Provisional Pat. App. No. 62/026,174, filed Jul. 18, 2014.

FIELD OF THE INVENTION

The present invention relates to implantable devices for achieving control over the size of emphysematous bullae during respiration. The device includes an elongated member having a fixed length, with at least one anchor on each end of the elongated member for implantation into the lung.

BACKGROUND

Emphysema is a form of chronic obstructive pulmonary disease (COPD) that is defined by abnormal and permanent enlargement of the airspaces distal to the terminal bronchioles and is associated with destruction of the alveolar walls. The destruction of alveolar walls causes loss of elastic recoil, early airway closure during exhalation, and air trapping in the distal air spaces. Alveolar wall destruction with formation of emphysematous blebs and bullae leads to loss of gas exchanging surface (also known as increased physiologic dead space). In addition, air trapping and hyperinflation press the diaphragm into a flat configuration, rather than its normal domed shape, and place all the muscles of respiration at a mechanical overstretch disadvantage. In combination, these processes lead to refractory dyspnea.

Lung volume reduction surgery (LVRS) is a surgical treatment for patients with advanced emphysema whose dyspnea is poorly controlled with the usual therapies (e.g., short and long acting bronchodilators, inhaled glucocorticoids, supplemental oxygen, and pulmonary rehabilitation). LVRS entails reducing the lung volume by wedge excisions of emphysematous tissue. However, surgical morbidity is high and non-pulmonary comorbidities may preclude surgery. Bronchoscopic lung volume reduction (BLVR) refers to techniques developed to treat hyperinflation due to emphysema via a flexible bronchoscope.

During the past few years, there has been great interest in bronchoscopic lung volume reduction using different designs of one-way valves as an alternative to lung volume reduction surgery. However, the efficacy of these treatments is limited by both the presence of collateral airflow from adjacent segments, which inhibits the volume reduction of the treated lobe, and the technical difficulty of accurately placing these one-way valves in difficult airways anatomy. However, some valve results showed that the patients with heterogeneous emphysema will not benefit from treatment with one-way valves, indicating the need for BLVR treatments that work independently of collateral flow and are less reliant on the very accurate placement of an air sealing device.

One previous attempt relied upon the use of LVR coils made from preformed wire, where the coil is delivered into subsegmental airways and recovers to a predetermined shape upon deployment. Additional coils are implanted as necessary, with each coil reverting to its twisted, entangled shape. The problem with this approach is that the coils may also entrap or ensnare portions of the lung parenchyma that still have regions or pockets of functional respiration within the bullae. There is presently a need to have a device that can prevent the formation of bullae without the necessity of lung volume reduction. A device that can prevent bullae formation without eliminating remnants of functional lung parenchyma is needed.

SUMMARY

The invention is related to an implantable device for control over the size of emphysematous bullae in a lung, including: an elongated central region having a fixed axial length; a first end including a first anchor; and a second end including a second anchor.

The invention also includes an assembly including the implantable device and a deployment device for placing the implantable device in a desired location.

The invention also includes a method of delivering the implantable device, including the steps of aligning the first anchor to a target site while the implantable device is at least partially placed within a deployment device, deploying the first anchor such that it engages a first region of the lung, pulling the first anchor in a proximal direction towards the second anchor, and releasing the second anchor such that it engages a second region of the lung.

BRIEF DESCRIPTION OF THE FIGURES

FIGS. 14A-14B show an alternate embodiment of a device with radially expanding fixation elements.

DETAILED DESCRIPTION

Figure 1A:
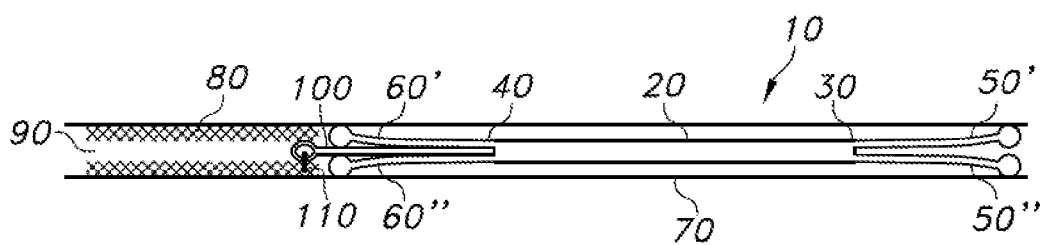
FIGS. 1A-1E show various stages of deployment of a device.

The present invention relates to an implantable device suitable to achieve Bronchoscopic lung volume reduction (BLVR) in a patient. The patient may be a mammal, such as a human. The implantable device is suitably delivered by a clinician, such as a surgeon. As used herein, the individual implanting the device will be referred to as the "clinician" or "user", and the location of implantation will be referred to as the "target site". The target site is desirably one or more spaces in the lung of the patient, such as a bronchiole or other region in the lung.

The device is generally an elongated device, having a first end, second end, and a central region. The central region is generally cylindrical in shape, and is desirably a semi-rigid material such that it will not be bent or flexed during normal respiration. As will be described below, the first and second ends may include flexible elements or shape memory elements. The relative rigidity of the elements is such that the first and second ends are more flexible than the central region. The elongated central region has a fixed length and remains substantially straight before, during and after implantation. The use of a straight, fixed length central region allows for implantation without folding of lung tissue and unnecessary exclusion of functional parenchyma from respiration. Different length devices are contemplated, to achieve different levels of reduction. Different diameter central regions can also be utilized to closely match the region of the lung targeted for treatment. For example, a smaller emphysematous region can be treated with a device having a smaller diameter central region and a larger emphysematous region could be treated with a device having a larger diameter. These decisions are made by the clinician (e.g., an interventional pulmonologist, physician or surgeon) and are based on a number of factors, including the size of the emphysematous region, the diameter of the bronchi used in deployment, and how distal the emphysematous region is in the respiratory tree.

At the first end and the second end is at least one anchor. The anchor is designed to be deployed within a region of the lung, such as a bronchiole, and after implantation, the anchor is securely implanted within the region into which it is implanted. It may be desirable that the anchor be free of traumatic elements, such as tissue piercing elements, although piercing elements may be used in some configurations.

In use, the clinician inserts the device through a suitable implantation means or deployment device, such as a catheter or bronchoscope, aligning the first end with the target site. The first end may be referred to as the distal end, since it is located distally from the clinician (as compared to the second end). In that respect, the second end may be referred to as the proximal end, since it is located more proximally to the clinician than the first end. After aligning the first end, the first end is released from the deployment device, where it engages the target site of the lung, including a bronchiole. The device is then pulled or compressed proximally. Since the first end is now securely engaged with tissue, pulling the device results in the section of the lung tissue being pulled or compressed or collapsed proximally. When the lung has been pulled or compressed to a desired length, the second end may be released from the deployment device, where it secures itself to a second region of the lung. The clinician performing the procedure will try to pull the device proximally to a point where the volume of the lung has been reduced to a desired dimension to allow for normal, better, or less restricted breathing. This is ascertained by imaging techniques known to one of ordinary skill in the art. Thus, the intent is not necessarily to cause complete collapse of the emphysematous region, but to reduce its volume to a size that will allow any remnants of functional alveoli to participate in respiration as well as prevent the excessive expansion seen in the original, untreated bullae.

Given the rigid, fixed length central region, the lung volume will be reduced to the extent that the lung tissue is pulled or compressed proximally, without the need for tethering, locking, or other means to secure the implanted device's length. Previous methods have relied upon the use of a string or other tethering device, which is used to pull multiple anchors. When such tethering devices are used, there is required a locking or other securement means when the implanted device has been pulled to a sufficient degree. With the present invention, the device has a fixed length, and therefore no adjustment of the device length, or securement of the device's length is required. The length of the implanted device is known, and there is greater assurance to the clinician of the implanted device's security.

Thus, the invention includes a device for controlling the volume of a portion of a lung, the device including an elongated central body having a fixed length, and the device having a proximal end and a distal end. The device includes at least one anchor at the proximal end of the body and at least one anchor at the distal end of the body. The anchors may take differing configurations, as will be described below. For example, in one configuration, the anchors have deformable members having a positioning configuration in a collapsed state and an anchoring configuration in an expanded state. The anchors include at least one engagement feature with an attachment means, to secure the anchor in the deployed position. The device may include non-tissue piercing engagement feature, and in some embodiments, the device may be removable after deployment.

Thus, the device includes, in its broadest sense, three components: a central region, a first end and a second end. The three components will now be described. The elongated central region may be a wire or may include a plurality of wires connected to each other at at least one connection point. The elongated central region is desirably substantially rigid, such that it will maintain its shape and length before, during and after deployment of the device. The central region may include imaging markers, such as radiopaque markers or fluorescent markers at one or more regions of the central region.

The elongated central region may have any cross-section desired, such as circular, triangular, square or rectangular. If the central region is made of a plurality of elongated elements, those elements may be arranged in a tight configuration, or may be arranged in a circular configuration with a hollow interior. The elongated central region may have any axial length (measured from first end to second end) desired, including about 1 cm to about 5 cm length, or alternatively about 1 to about 3 cm length, and about 0.1 mm to about 2 mm diameter or about 0.3 mm to about 1 mm in diameter. The central region may be solid or may have a hollow axial interior (e.g., a tube).

The first end and the second end include at least one anchor. The anchor or anchors at the first end and the second end may be the same or they may be different. The anchors may be formed from the same material as the elongated central body, or they may be separate components that are secured to the central body. In some embodiments, the elongated central body is a unitary structure, and the anchors at the first and second end are formed by longitudinal segments formed in the central body at least at one end thereof by longitudinal cuts. In other embodiments, the central body may include a plurality of linear members joined lengthwise at at least one connection point, and the anchors are formed from the linear members at the first and the second ends.

The anchors at the first and/or second ends may have any desired configuration, where the anchors are sized and shaped to be deployed within the target site and be secured there via tissue engaging or contacting feature or features. As noted above, the anchors and the tissue-contacting feature at the first and second ends may be the same or may be different. The tissue-contacting (or tissue-engaging) features may include features such as barbs, balls, roughened surfaces, hinged arms, shape memory materials, and combinations thereof.

In one embodiment, the first and second ends include shape memory materials, where in a collapsed state the anchors extend axially along the axial length of the central elongated region, but when released from the collapsed state, the anchors curl or move to be substantially perpendicular to the axis, or to be facing the opposite axial direction. An anchor may be curled in the shape of a semi-circular or semi-elliptical configuration, approximating a segment of a circle or ellipse to any degree desired. The degree of curvature of the anchors may be from about 25 degrees to about 180 degrees, or from about 45 degrees to about 120 degrees. In some embodiments, an anchor may have a degree of curvature of about 60 to about 90 degrees.

For example, FIGS. 1A-1E depict various stages of deployment of a device from a catheter. In this embodiment, the device 10 includes a central body 20, which is elongated and includes a distal end 30 and a proximal end 40. The central body 20 maintains its axial length (defined as the length between distal end 30 and proximal end 40) during implantation and after implantation. The device includes and anchor at the distal end 30, and in this embodiment, the anchor includes a first shape memory element 50' and a second shape memory element 50". The device in this embodiment includes an anchor at the proximal end 40, as well, where the anchor at the proximal end 40 includes a first shape memory element 60' and second shape memory element 60". As depicted in FIGS. 1A-1E, the shape memory elements (50, 60) expand outward approximately to about 45 degrees. Also, in this embodiment, the shape memory elements 50, 60 include ball-like members on their ends, which are intended to reduce trauma and allow for repositioning if desired. Other ends as described above may be used. Further, more or less shape memory elements may be used at each end, if desired.

Before deployment, the device 10 is housed within a catheter 70, or other elongated device shaped and sized to house the device 10. The device 10 is housed within the catheter 70 in such a fashion that the shape memory elements 50, 60 are compressed. Within the catheter 70 is a positioning element 80, which is disposed at the proximal end 40 of the device 10. The positioning element 80 may include a central opening 90, if desired. The proximal end 40 of the device 10 includes an engagement member 100 or other device, which is removably secured to an attachment 110 located at the distal end of the positioning element. The engagement member 100 may be a string or tether with a hook or eyelet at the proximal end, where the hook or eyelet engages with the attachment 110 of the positioning member 80. For example, the engagement member 100 may include an eyelet or ring, which is fitted onto a hook of the attachment 110. Removal of the engagement member 100 from the attachment 110 may be achieved by sliding the eyelet or ring of the engagement member 100 off of the attachment 110. In some embodiments, the engagement member 100 may have a magnetized end, which may be secured to an attractive element on the attachment 110. Other removable connections for the engagement member 100 and attachment 110 may be used as desired.

Figure 1B:
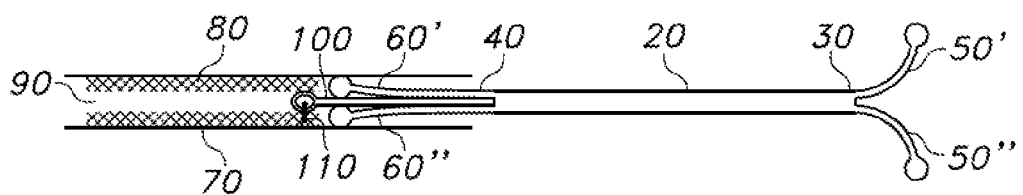

As seen in FIG. 1B, the catheter 70 is pulled proximally, while the positioning member is maintained in its position. The positioning member restricts the device 10 from being pulled with the catheter 70, and thus the distal end 30 of the device 10 is released from the catheter 70. Upon release from the catheter 70, the first shape memory elements 50', 50" are allowed to expand to their desired position. When the device 10 is implanted into a body or organ, the expansion of the first shape memory elements 50', 50" allows the shape memory elements 50', 50" to be secured into openings in the tissue of the body or organ. At this point, the elements at the proximal end 40 of the device 10 have not been released from the catheter 70. If desired, the catheter may be advanced distally again, compressing the first shape memory elements 50', 50", and allowing re-positioning of the device 10.

Figure 1C:
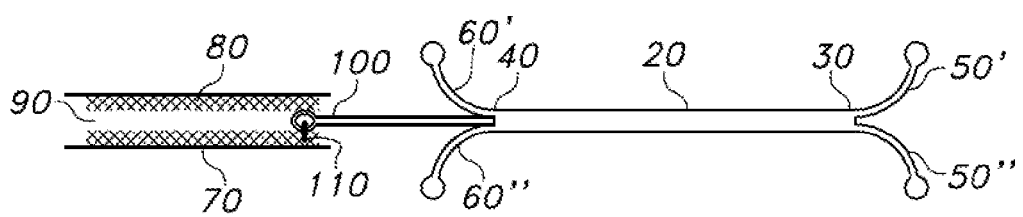
Figure 1D:
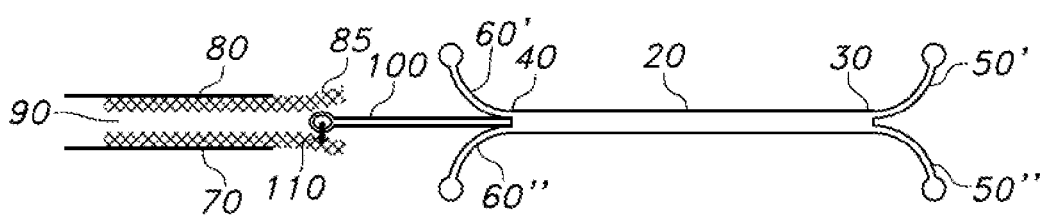

If the device 10 is positioned properly, the catheter 70 may continue to be withdrawn proximally, as seen in FIG. 1C, thereby releasing the second shape memory elements 60', 60". Also as seen in this Figure, the second shape memory elements 60', 60" include ball-like members on their ends, but other ends described above may be used. It is desired that distal engagement members, such as shape memory elements 50', 50" at the distal end 30 are configured to engage tissue and hold tissue when pulled in the proximal direction. Similarly, it is desired that proximal tissue-engaging or tissue-contacting members, such as shape memory elements 60', 60" at the proximal end 40 are configured to engage tissue and hold tissue when pulled in the distal direction.

At this stage, the anchors of the device 10 have been released and are capable of grasping tissue, enabling the device 10 to be pulled and pull tissue in an opposite direction (e.g., distal anchors can pull tissue proximally and vice versa). The positioning member 80 is still secured to the device 10, since the engagement member 100 is still secured to the attachment 110 of the positioning member. Since the engagement member 100 is secured to the positioning member 80, the positioning member 80 may be pulled proximally, thereby pulling the distal end 30 of the device 10 in the proximal direction, and pulling any tissue into which the anchor of the distal end 30 of the device is secured, as well. The user may pull the distal end 30 (and also any tissue secured thereto) to any desired compressed length.

Figure 1E:
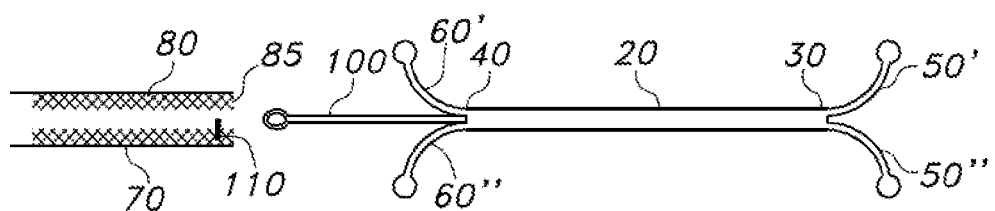

When the device is positioned and pulled to the desired length, the engagement feature 100 may be released from the attachment 110. In one embodiment, the distal end 85 of the positioning member 80 may be opened, allowing release of the engagement feature 100 (seen in FIG. 1D). The engagement feature 100 may be severed from the attachment 110, in some embodiments. FIG. 1E shows the device 10 after it has been released from the catheter 70 and the engagement feature 100 has been released and/or severed from the attachment 110. If desired, the engagement feature 100 may be severed at a location closer to the central body 20.

Figure 2:
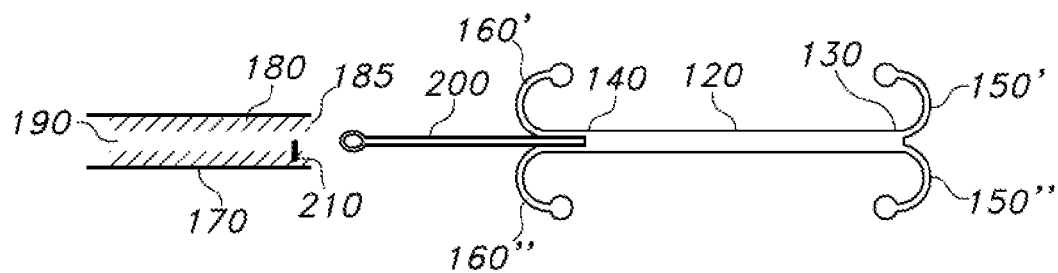
FIG. 2 shows an alternate device in a deployed state.

FIG. 2 depicts an alternate device as released from a delivery device, such as a catheter, but in this Figure, the shape memory elements have a greater degree of curvature (a smaller radius) in the absence of force thereon, such as after deployment. As can be seen, the device includes the elongated central body 120, with distal end 130 and proximal end 140, as described above. The distal end 130 includes at least one, and desirably at least two engagement members, which may be shape memory elements 150', 150". Proximal end 140 may include at least one, and desirably at least two engagement members, which may be shape memory elements 160', 160". Engagement members may be the same or may be different from each other. It is desired that distal engagement members, such as shape memory elements 150', 150" at the distal end 130 are configured to engage tissue and hold tissue when pulled in the proximal direction. Similarly, it is desired that proximal engagement members, such as shape memory elements 160', 160" at the proximal end 140 are configured to engage tissue and hold tissue when pulled in the distal direction. In this fashion, anchors or tissue engaging features can anchor to the tissue into which they are implanted, such that the device can be pulled in the opposite direction and pull the tissue along with it. That is, distal anchors enable tissue to be pulled proximally and vice versa. Further, tissue-engaging features such as anchors enable holding of the tissue in place, such as in a compressed state, after full deployment of the device.

The device in FIG. 2 may be released from the delivery device, such as catheter 170, having positioning member 180 with a distal end 185 and central opening 190. The catheter may have an attachment 210 secured thereto, to which an engagement feature 200 may be secured during implantation and positioning of the device.

Figure 3:
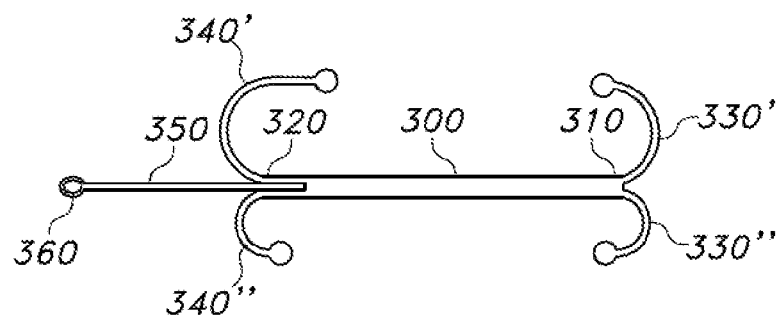
FIG. 3 shows an alternate device in a deployed state.
Figure 4:
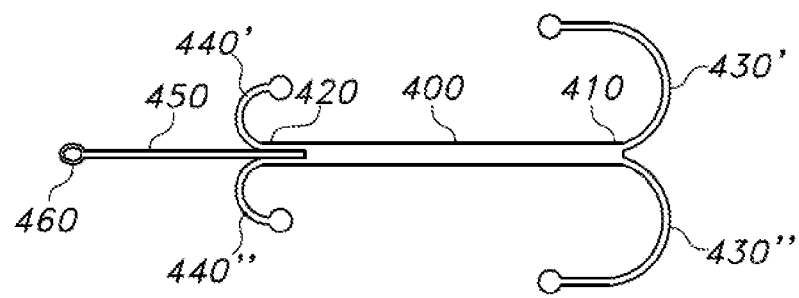
FIG. 4 shows an alternate device in a deployed state.
Figure 5:
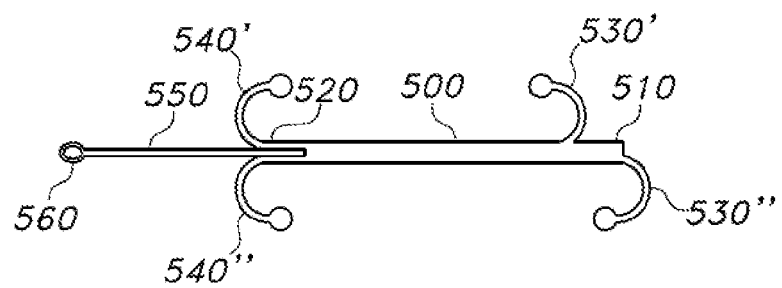
FIG. 5 shows an alternate device in a deployed state.

If a plurality of shape memory members or other engagement feature are used as an anchor, the shape memory members may take various forms and configurations. For example, one member may have a different size, shape, degree of curvature, or end feature than another member at the same end or at a different end. By way of non-limiting example, FIGS. 3-5 show several suitable configurations that would be useful in the present invention. FIG. 3, for example, shows a device with elongated central body 300 defined by distal end 310 and proximal end 320, with a plurality of shape memory elements 330', 330" at the distal end and plurality of shape memory elements 340', 340" at the proximal end. In this embodiment, it can be seen that each end has at least two differently configured members. At the distal end 310, shape memory element 330' has a broader curvature than shape memory element 330". A broader curvature may aid in grasping a larger volume of tissue in use. In this embodiment, shape memory element 340' has a greater overall length than shape memory element 340", such that the base of its curve extends more proximal (with respect to the central axis of the device) and the end of the element 340' extends more distal than the second shape memory element 340".

In FIG. 4, each end (distal end 410 and proximal end 420, respectively) has a pair of substantially identical elements, but the elements at the distal end 410 (elements 430', 430") differ in configuration than the elements at the proximal end 420 (elements 440', 440").

FIG. 5 depicts a configuration whereby the elements at one end are displaced from each other axially. That is, the device includes distal end 510 with at least two shape memory elements 530', 530". Shape memory element 530' extends from the device at a different axial location than shape memory element 530", and each has an end that is off-set from each other with respect to the central axis of the device.

It is desirable that each of the aforementioned designs and configurations includes an engagement feature (350, 450, 550) with securement end (360, 460, 560), where the securement end can be removably secured to a delivery device, to facilitate implantation and placement of the device in the proper tissue region. As can be seen, the anchors on each end may be the same or different from each other, or each anchor may have a plurality of gripping or tissue-contacting feature, where each tissue contacting feature is different from other tissue-contacting features at the same end or at the opposing end. The shape memory elements may have a number of different physical characteristics, include varying lengths, curvature radii, axial displacement, and combinations thereof.

Figure 6:
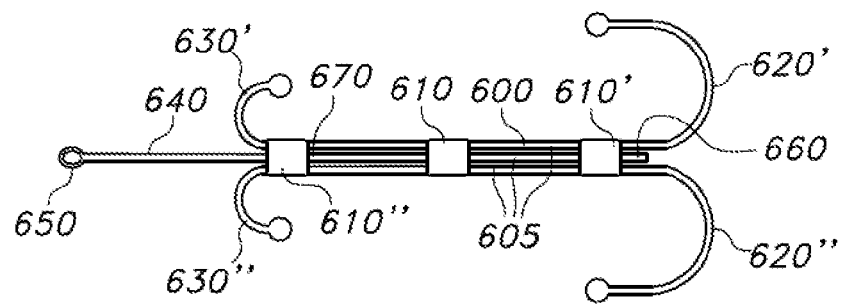
FIG. 6 shows an alternate device with attachment regions in a deployed state.

FIG. 6 depicts an embodiment of an implantable device that includes a plurality of elongated elements 605 forming the elongated central body 600, where the central body 600 is axially defined by distal end 660 and proximal end 670. In this aspect, each end (distal and proximal) includes at least one, and desirably a plurality of anchor members 620, 630. To maintain the multiple elongated elements 605 secured to each other, there may be at least one and more desirably a plurality of connection points 610 in the device. As seen in FIG. 6, there are three connection points, with a central connection point 610, a distal connection point 610' and a proximal connection point 610". More or less connection points may be used as desired. For example, there may be from one to about 10 points of connection along the central body 600. The points of connection 610 may include, for example, welded regions, tied regions, banded regions, and the like. The use of a plurality of elongated elements 605 may be useful in improving strength of the device, but also allowing a fluid channel through and around the central body 600. As with above, the device includes engagement feature 640 and an eyelet or other securing portion 650 to hold the device in the delivery apparatus until placement is achieved. The engagement feature 640 and securing portion 650 may be a hook and eyelet, or they may be attractable portions (such as through a magnet on one or both), or any other removable or severable attachment means.

Figure 7A:
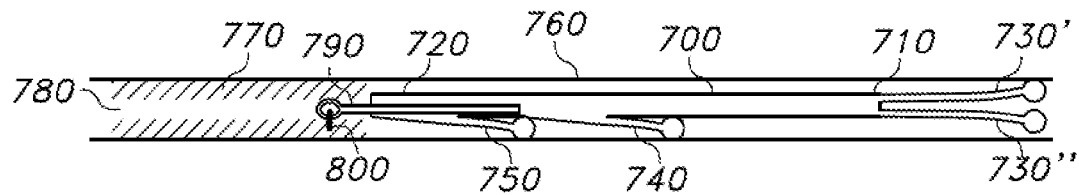
FIGS. 7A-7C show various stages of deployment of an alternative device.
Figure 7B:
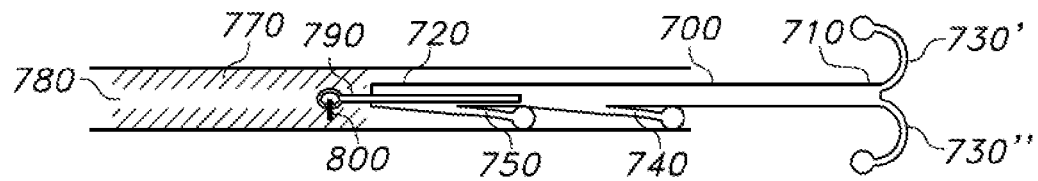
Figure 7C:
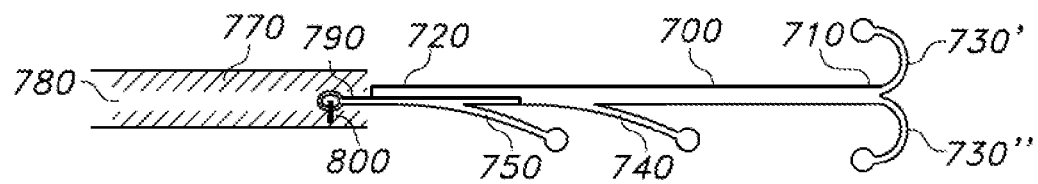

FIGS. 7A-7C show alternate embodiments, which include anchoring members that have a different configuration than the embodiments seen above. As can be seen in these Figures, the anchors may include at least one hinged arm, where the hinged arm faces towards the opposite end but is not curved at the angles described above. For example, if a hinged arm is placed at the first end, the hinged arm may face axially towards the second end. The hinged arm may have any angle (as measured between the longitudinal axis of the central body and the hinged arm) of from about 0 to about 50 degrees in a collapsed state, and about 10 to about 90 degrees in an extended state. As seen in FIGS. 7A-7C, the hinged arm 740, 750 may extend from the central body 700 at the proximal end 720, distal end 710, or therebetween. Any number of hinged arms may be useful in the present invention, such as from 1 to about 10. As noted above, the end of the hinged arm, as with the shape memory elements above, may have any feature, including atraumatic features such as balls or blunted ends. Alternatively, it may include a piercing or tissue-penetrating element, such as a needle, barb, hook or other element.

Deployment of a device including a first end having hinged arms and a second end including curling shape memory anchors is seen in FIGS. 7A-7C. FIG. 7A depicts the device in a collapsed state, as it is contained within a delivery device 760, such as a catheter. The delivery device 760 includes an outer sheath and a placement device 770, with elongated central region 780. The placement device 770 includes a distal end, at which the device is secured. Securement may be via engagement feature 790 and attachment 800, as described above. The device in collapsed state is introduced into the body into the tissue in which the device is to be implanted. The catheter 760 sheath is withdrawn in the proximal direction, allowing the distal end 710, with its anchor(s) 730, to be free from the catheter's constraint. In this embodiment, the shape memory elements 730 are free to take the unencumbered shape, such as the various configurations described above. The shape memory elements 730 engage tissue into which the device is implanted, and the device may be pulled proximally (such as by pulling on the attachment 800, which pulls the engagement feature 790, pulling the entire device proximally). This pulls or compresses or collapses tissue along with the device, given the shape and configuration of the shape memory elements 730 at the distal end 710.

Once the distal end 710 is placed and tissue is pulled (if desired), the catheter 760 is pulled further proximally while the device is held in place, revealing any other anchors on device body 700. As seen in FIG. 7C, upon retraction of the catheter 760 sheath, anchor members (here, hinged arms 740, 750) are freed from the constraint of the catheter 760 and allowed to expand to their unencumbered configuration. Since the device is still secured to the catheter 760 and placement member 770, the device may be pulled proximally or may be pushed distally. Since the anchors in the device (e.g., 730, 740, 750) are expanded and allowed to engage tissue, pulling and/or pushing the device moves and compresses the respective tissue. Tissue may be collapsed by pulling the device proximally, and upon release of the proximal anchors (740, 750), collapsed tissue between the distal end 710 and proximal end 720 may be trapped and held in the collapsed state. In addition, if non-traumatic ends are used, the catheter 760 sheath may be placed back over the device, collapsing any anchors and freeing the tissue held therein, and the device may be moved or replaced into a different position.

The device may be moved into final position, and the engagement feature 790 may be severed or otherwise disconnected or released.

As can be seen in the above Figures, the anchors or other tissue-engaging or tissue-contacting features may be atraumatic and/or non-tissue piercing. The ends may be rounded, ball-like ends as seen above, or they may simply be smooth, blunted non-piercing ends. The tip of the engagement feature may be, for example, a hook, a ring, a ball, an ellipsoid, a disk, or a tab. The tip of the anchor engagement feature may have a thickness that is greater than the anchor wire or central body thickness. It is contemplated, however, that the ends of the engagement feature may include a tissue engaging or tissue piercing element, if such anchoring is desired. In such embodiments, the configurations described and seen above may have at least one tissue piercing end. The anchors may include only one engagement feature (i.e., one hinged portion) or they may include a plurality of engagement feature (i.e., two or more hinged portions).

Further, the anchors may have various combinations of piercing, non-piercing, hinge, curling, and other tissue-engaging or tissue contacting features. Thus, a device may have, for example, a first end that includes two curled non-piercing tissue-engaging or tissue contacting features, and a second end that has one curled non-piercing tissue-engaging or tissue contacting features. Another device may include a first end having at least one curled non-piercing tissue-engaging or tissue contacting features, while the second end includes at least one hinged, tissue-piercing tissue-engaging or tissue contacting features. In some embodiments, the device may include a first end having at least one curled tissue-engaging or tissue contacting features and at least one hinged tissue-engaging or tissue contacting features, and a second end having at least one hinged tissue-engaging or tissue contacting features and/or at least one curled tissue-engaging or tissue contacting features.

Figure 8:
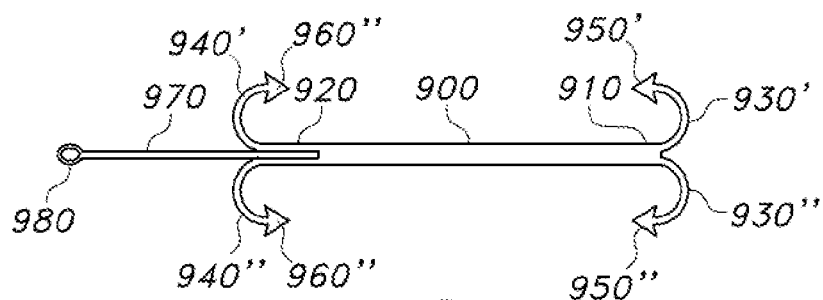
FIG. 8 shows an alternate device in a deployed state.
Figure 9:
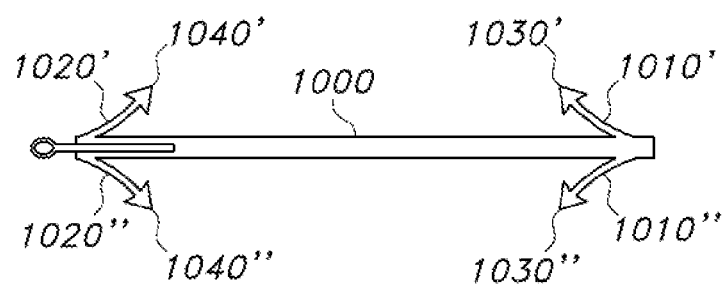
FIG. 9 shows an alternate device in a deployed state.
Figure 10:
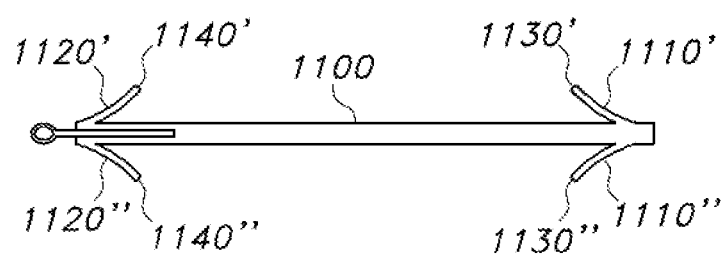
FIG. 10 shows an alternate device in a deployed state.
Figure 11:
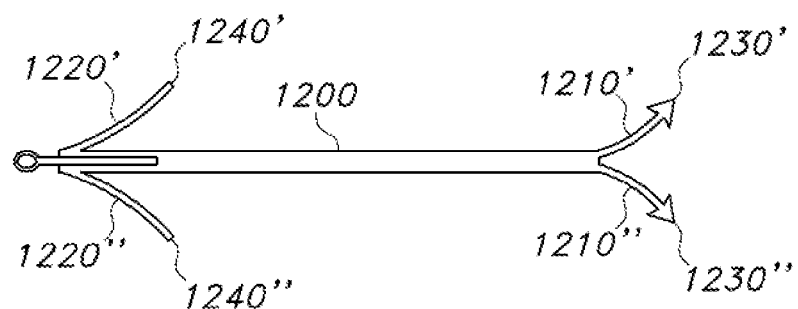
FIG. 11 shows an alternate device in a deployed state.
Figure 12:
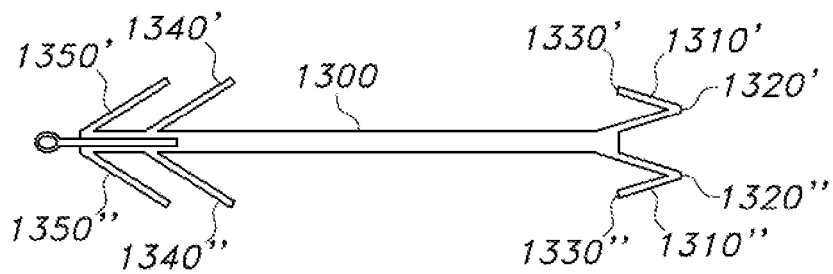
FIG. 12 shows an alternate device in a deployed state.

For example, FIGS. 8-12 depict various configurations that include combinations of curved members, hinged members, penetrating members and non-penetrating members. Each of these figures includes the central body axially defined by a proximal end and distal end, with anchor members at the proximal and distal ends. Each also includes an engagement feature at the proximal end, which is to be secured to an attachment in a delivery device for placement and pulling the device in tissue. FIG. 8, for example, shows a plurality of hooked shape memory elements, with at least two elements 930', 930" at the distal end 910, and at least two elements 940', 940" at the proximal end 920. At the end of each of the distal elements 930', 930", there is a tissue-penetrating hook 950 or other piercing member. At the end of the proximal elements 940', 940", there is also a tissue penetrating hook 960 or other piercing member. FIG. 9 shows hinged arms (1010, 1020) with tissue-penetrating elements (1030, 1040) on each hinged arm. FIG. 10 shows hinged arms 1110, 1120 with ends that are non-tissue-penetrating (1130, 1140). FIG. 11 shows a pair of distal end elements 1210', 1210", each of which has a hook or barb 1230 at its end. In this embodiment, the distal end elements 1210 may extend substantially distally, while the hook or barb 1230 may face the proximal end (allowing it to engage tissue and enabling it to pull such tissue proximally). FIG. 12 shows a proximal end with four hinged arms 1350, 1340, and a distal end with a multi-angled configuration. The multi angled configuration in this embodiment has anchors 1310', 1310" each with a bend 1320 and an end 1330. The end 1330 faces in the proximal direction, again, allowing for it to engage tissue and allowing the device to pull such tissue proximally after implantation.

Any combinations of the above anchor configurations may be used. The anchors may have tissue contacting or tissue engaging features arranged in any desired configuration including penetrating ends or non-penetrating ends, rounded curvatures, hinges, longer or shorter lengths, multi-angled configurations, or barbs that face an opposing direction. In addition, these members or anchors may be disposed at either axial end of the device, or they may be disposed on the side wall of the elongated body at a more central region than either the distal or proximal end. If multiple tissue contacting or tissue engaging features are used, they may each be disposed on the axial end, or they may be disposed on the side wall of the elongated body. They may be disposed circumferentially spaced about the body, or they may be offset from each other. They may be helically disposed or linearly disposed. The anchors and tissue contacting or tissue engaging features may be disposed at the same position(s) on the first end as they are on the second end.

The anchor lengths may be any size desired, and in some embodiments, the anchor length may be from about 10% to about 25% to about 50% or up to 100% of the axial length of the central elongated body. Anchors at the distal end may be larger in size, shape, length, or thickness as anchors at the proximal end, or anchors at the proximal end may be larger in size, shape, length, or thickness as anchors at the distal end, or they may be the same size, shape, length or thickness.

Delivery of the device may be achieved through a catheter or other similar delivery device having a sheath that can hold and compress the device in a collapsed state. During delivery, the device and its anchors are held in a collapsed configuration within the delivery device. Upon alignment of the distal end at the target site within tissue, a pushing means may be used to deploy the first end such that it is engaged and secured to the target site. The pushing means may push the device distally, or it may hold the device in place while the outer sheath is moved proximally. The distal end, and any anchor members thereon, is released from the outer sheath, allowing the anchors to take their unencumbered shape and engage tissue. The device may be pulled proximally, so as to pull the tissue in which the distal end is engaged, and then the catheter sheath may be withdrawn proximally to a greater extent, releasing any anchors along the central body. Finally, the device is fully released from the sheath, and any anchors at the proximal end are released from the catheter sheath. Releasing the proximal end causes any anchors thereon to take their unencumbered configuration and secure themselves to the target site tissue at the site of release.

The device and anchors, with tissue contacting or tissue engaging features, may be disposed and implanted through any desired means, including, for example, a pushing means. Alternatively, they may be disposed with a grasping device, which includes a connector means or a release mechanism, such as the release of a sheath or catheter. The device anchors may be implanted by a grasping element having a tether or other type of release. The device may be released through a screw-type device, or a hook and loop type of mechanism. It may be desired that the device be capable of being retrieved by the deployment mechanism, such that it may be removed or replaced if needed. A connector portion of the deployment device may include a grasping element designed to grasp a portion of one end of the implantable device.

Ultimate release of the device from the delivery device may be achieved by releasing or severing an engagement feature, which is secured to an attachment in the body of the delivery device. For example, the engagement feature may be a tether that is physically connected to the device and is secured to an attachment, such as an eyelet or other feature in the delivery device. Release may also be achieved by rotational engagement, where rotation of a connector feature disengages the connector feature from the implantable device, or by screw engagement, or by release of compression, or any other desired release methods.

Figure 13A:
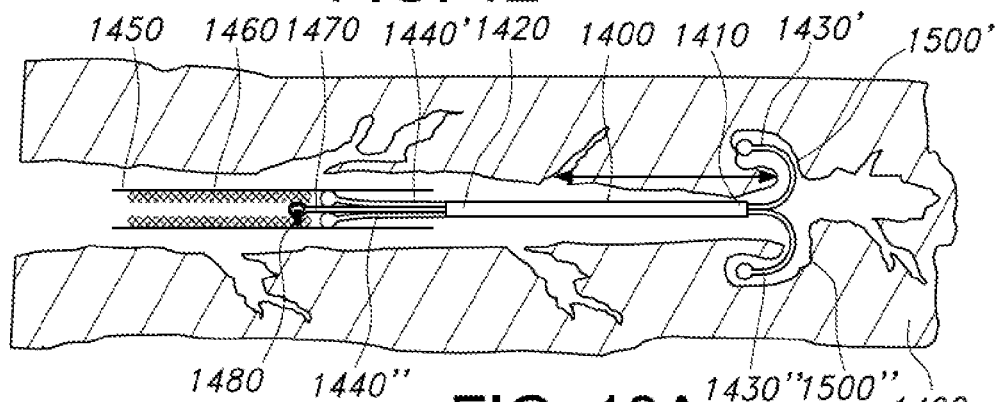
FIGS. 13A-13C show various stages of deployment of a device within a lung.
Figure 13B:
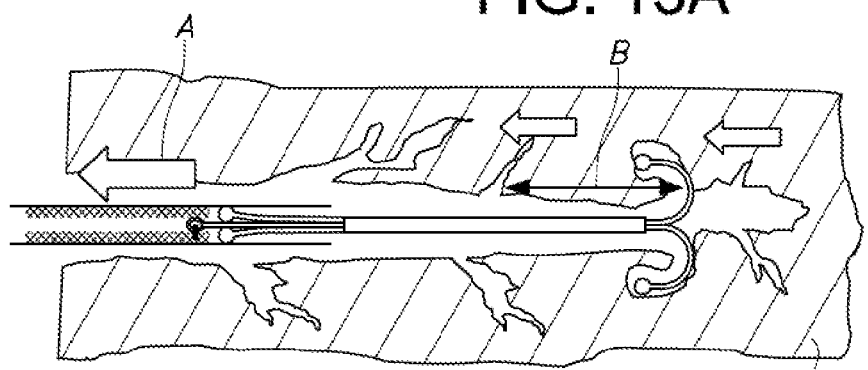
Figure 13C:
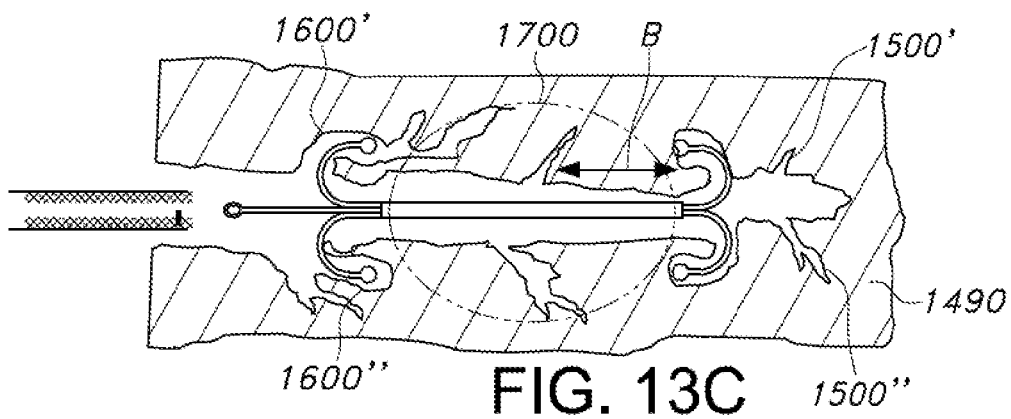

The present invention includes a method of compressing the volume of a portion of soft tissue, such as a portion of a lung. The devices described above may be useful in this method. FIGS. 13A-13C show several steps of this method. FIG. 13A shows the device as it is being implanted into a desired region of the lung, with the distal end already released from the catheter sheath. The desired region into which it is implanted may be a diseased region of a lung such as an emphysematous bullae, or may be a healthy region of a lung. FIG. 13B shows the movement of the implantable device in a proximal direction (direction "A"), pulling tissue engaged with the distal anchor element(s). FIG. 13C shows the release of the proximal end of the implantable device after the tissue has been moved proximally. For this description, the implantable device includes an elongated central body 1400, which is axially defined by a proximal end 1420 and distal end 1410, with anchor members on each end. In this description, the distal anchor members 1430', 1430" are atraumatic anchors with a 180 degree curvature, and the proximal anchor members 1440', 1440" are similarly atraumatic anchors with a 180 degree curvature. It is understood that any alternative configurations described above may be used in this method, but for simplicity and ease of understanding, only this configuration will be used in the following description.

The method first includes the step of identifying the portion of the tissue that is to be compressed. That portion may include, for example, a diseased portion of the lung. The implantable device, which may have the configurations described above (which generally includes an elongated central region having a central axis, which is defined by a proximal and distal end, each end having an anchor, which may include one or more shape memory elements) is placed into a deployment device, such as a catheter with a lumen sized to accommodate the device. While contained within the sheath of the catheter, the implantable device is in a collapsed or compressed state, where the anchor elements thereon are in a temporary state of compression under force.

The implantable device is engaged with a positioning member (also known as a pushing member) while in the deployment device, the positioning member including an element sized to fit inside the catheter and the positioning member having a connector attachment adapted to releasably engage with the implantable device. The connector attachment may be secured to the engagement feature(s) of the implantable device. In one embodiment, the connector attachment is an eyelet or other threadable element, and the engagement feature is a tether connected to the proximal end of the implantable device, which can be secured to the connector attachment. The connector attachment and the tether may be releasably connected via other means, such as through the use of magnets or other connection. The positioning member may be at least partially enclosed within the outer sheath of the catheter, capable of being axially slidable in the proximal or distal directions, and the implantable device is disposed distally of the positioning member. The positioning member and the catheter may be axially slidable or displaceable with respect to each other. The positioning member may have an axial opening, into which the engagement feature of the implantable device can be placed. The use of an axial opening in the positioning member allows for a user to grip or otherwise contact the engagement feature during implantation. It is desired that the proximal end of the implantable device be at least partially in contacted with the distal end of the positioning member, so as to allow the positioning member to push the implantable device distally or to hold it in place during implantation.

The method includes the step of advancing the deployment device into the desired tissue region, and releasing the distal end of the device from the deployment device, thus allowing any anchor elements at the distal end of the implantable device to return to their permanent shape and configuration within a target site in the tissue. Release of the distal end may be achieved by holding the device in place by the positioning member, and sliding the catheter proximally, or it may be achieved by holding the catheter in place and pushing the device distally. The distal end of the implantable device is released from the catheter and the anchor element or elements are free to take their unencumbered shape, as explained above.

The distal anchor element(s), now secured in the target tissue (such as lung parenchyma and distal bronchia wall), as can be seen in FIG. 13A. By pulling the implantable device proximally, the tissue into which the distal anchor(s) is secured is moved in the proximal direction (A). Arrow B indicates compression of tissue upon pulling device proximally, with shorter length of arrow B indicating tissue is compressed. Based on imaging of the lung obtained by a visual means, such as an endoscope, CT scan, MRI, ultrasound, and the like, a user, such as a physician, may decide to pull the implantable device more or less proximally until it reaches a point that reduces the emphysematous bullae to the desired degree. This movement of tissue can be seen in FIG. 13B. Thus, the method includes the step of compressing a section of tissue by pulling the implantable device towards a proximal end. Once the tissue has been pulled to the desired length, the proximal end of the implantable device can be positioned in the desired location in the tissue. The proximal end of the implantable device, and any anchor elements thereon, may be released from the catheter sheath. As with the distal end, release of the proximal end may be achieved by holding the device in place by the positioning member, and sliding the catheter proximally, or it may be achieved by holding the catheter in place and pushing the implantable device distally. The proximal end of the implantable device is released from the catheter and the anchor element or elements are free to take their unencumbered shape, as explained above. If any anchor elements are disposed along the axial length of the central body, they are released sequentially as the catheter is moved proximally with respect to the implantable device. In some embodiments, the step of pulling the implantable device proximally after the distal anchor element(s) are released need not be performed, such as in the deployment into a deflated lung.

Once proximal end of the implantable device is released from the catheter and the anchor element or elements are free to take their unencumbered shape, the anchor elements engage the tissue into which they are implanted. Optionally, the implantable device may be moved in any direction, since the device is still secured to the positioning member by contact and also the attachment is still secured to the engagement feature.

Finally, the method includes the step of disengaging the implantable device from the positioning member. Disengaging may include, for example, severing the engagement feature, untying the engagement feature, disconnecting magnets or other holding device, or otherwise separating the engagement feature from the attachment.

The present invention may include a kit, which includes the implantable device as explained above (which includes an elongated central region, and a proximal and distal end, each end having an anchor element), a deployment device, which may include an elongated catheter with a lumen sized to accommodate and compress the implantable device into a collapsed state, and a positioning member sized to be slidably fit inside the catheter and having an attachment adapted to releasably engage with an engagement member of the implantable device. For example, the attachment may be releasably engaged with a proximal and/or distal engagement feature of the device. The various components may be packaged together or may be packaged separately. Further, the invention includes an assembly including the implantable device and the deployment device, with the positioning member therewithin.

The anchor elements may be metal or polymeric. In one embodiment, the anchor elements are comprised of nitinol. In one embodiment, the anchor elements have protrusions or roughened surfaces from their outer surface to engage surrounding tissue so as to secure them in place, or the anchor elements may be free of tissue-penetrating elements.

The present invention differs from prior attempts using a coiled device in that the clinician needs only to pull the inventive device proximally after the distal anchor is deployed. The amount of pulling or tissue compression can be at the discretion of the clinician, and is preferably guided by imaging techniques. In addition, the axial length region of the inventive device can be varied, i.e., many lengths can be provided to tailor the procedure to anatomical dimensions and surgical need. The various materials, including the implantable device, may be MRI compatible.

One embodiment of the invention may include the distal end and proximal end of the implantable device being interconnected by a ratcheting connector, with adjustability of the implantable device length and additional tissue compression capability. In another embodiment, the distal and proximal ends may be connected by a string or tether, such that the tether comprises the elongated central body of the implantable device. In embodiments where the elongated central body is hollow, a string or tether may be fed through the center of the elongated central body for attachment to deployment device. For a hollow tubular central body, anchors may be formed from walls of the tubular body, such as by forming axial slits in the tubular body and bending resulting strips of material forming deployable anchors.

In yet another embodiment, the elongated central body of the device may include or consist of a tensioner spring between the distal anchor elements and the proximal anchor elements. The spring may extend the entire axial distance therebetween or a part of the elongated body. The use of a spring may enable further tensioning of the implantable device just before releasing the distal anchor elements from the deployment implantable device, thus resulting in further compression of tissue, and a spring may offer some lateral deformation mobility or elastic bending. It is preferred, however, that the axial length of the device from proximal end to distal end remains constant.

There may be included magnetic interactions of deployed anchor elements. In one embodiment, the magnets are rare earth magnets. The anchor elements may be encased within a silicone or other elastomer known to be biocompatible and stable within the body, i.e., non-resorbable. The casing may include a radiopaque material such as barium. In one embodiment, the encased magnet has pointed edges or barbs on its outer surface so as to engage surrounding tissue such as bronchial wall or lung parenchyma. The implantable devices may be deployed in different bronchial paths at a point as distal as possible.

In some methods, vacuum may be applied to the region of the lung being treated so as to induce the sections of the lung towards one another.

FIGS. 14A-14B show an alternate configuration for an implantable device, which has an elongated central region 2000 with a fixed axial length, the central region 2000 having proximal end 2010 and distal end 2020. At each end, there is a fixation element, with proximal fixation element 2030 located at the proximal end 2010, and distal fixation element 2040 located at the distal end 2020. In this embodiment, the fixation elements 2030, 2040 are radially-expanding elements, which include a series of shape-memory elements that have a radially-expanding central region. In FIG. 14A, it can be seen that the proximal fixation element 2030 is expanded, while the distal fixation element 2040 is compressed. Although not seen in this Figure, the distal fixation element 2040 is compressed through application of some force or energy, such as by being compressed in a catheter or deployment tube, as explained above. In some embodiments, the device may be compressed until energy, such as heat or other stimulus, is applied thereto. FIG. 14B shows the distal fixation element 2040 in expanded state. When the fixation elements are in their expanded states, the force expanded outwardly presses the fixation elements against the tissue into which they are applied, holding them in place. The surfaces of the fixation elements 2030, 2040 may be roughened or have gripping elements, such as barbs or protrusions to aid in fixation in tissue. The elongated central region 2000 may be tubular and hollow, or it may be solid, or it may have passageways or channels through which fluid may flow. Engagement member (not shown in FIG. 14) is positioned at proximal end of central region 2000.

The invention claimed is:

1. A method of delivering an implantable device to a target site in a lung of a patient, the implantable device comprising:
   (a) an elongated central body having a fixed axial length such that the elongated central body rigidly extends along a longitudinal axis;
   (b) a distal end including a first anchor; and
   (c) a proximal end including a second anchor;
   the method comprising the steps of:

(a) aligning the first anchor to the target site while the implantable device is at least partially placed within a deployment device;
(b) deploying the first anchor by flexibly deforming the first anchor outwardly relative to the longitudinal axis such that the first anchor engages a first region of the target site of the lung;
(c) pulling the first anchor in a proximal direction towards the second anchor to reduce the volume of the lung; and
(d) severing an engagement feature, untying the engagement feature, or disconnecting magnets of the engagement feature to flexibly deform the second anchor outwardly relative to the longitudinal axis from a first position to a second position such that the second anchor engages a second region of the target site of the lung, wherein the second position is distal to the first position.

2. The method of claim 1, further comprising the step of obtaining an image of a diseased area of the target site.

3. The method of claim 1, wherein the target site is a one or more spaces of the lung.

4. The method of claim 1, wherein the target site is a bronchiole in the lung.

5. The method of claim 1, wherein pulling the implantable device proximally treats Emphysema.

6. The method of claim 1, wherein the elongated central body is rigid, wherein the pulling step reduces lung volume to the extent that the first region of the target site is pulled or compressed proximally.

7. The method of claim 1, wherein the target site is at least one emphysematous bullae, wherein the pulling step controls the size of the emphysematous bullae in the lung.

8. The method of claim 1, wherein the target site is an emphysematous region, wherein the pulling step does not completely collapse the emphysematous region of the lung.

9. The method of claim 1, wherein pulling the implantable device proximally treats chronic obstructive pulmonary disease by reducing the size of the lung to allow remnants of functional alveoli to participate in respiration and prevent excessive expansion seen in untreated bullae.

10. The method of claim 1, wherein deploying the first anchor by flexibly deforming the first anchor outwardly relative to the longitudinal axis further comprises releasing the first anchor by flexibly deforming the first anchor outwardly relative to the longitudinal axis to have a degree of curvature from about 25 degrees to about 180 degrees relative to the longitudinal axis.

11. The method of claim 1, the second position has a degree of curvature from about 25 degrees to about 180 degrees relative to the longitudinal axis.

12. The method of claim 1, wherein at least one of the first and second anchors comprise barbs, balls, roughened surfaces, hinged arms, or shape memory materials.

13. The method of claim 1, wherein deploying the first anchor further comprises deploying first and second arms of the first anchor by selectively transitioning the first and second arms of the first anchor outwardly relative to the longitudinal axis such that the first and second arms of the first anchor engage the first region of the target site of the lung, and wherein pulling the first anchor in the proximal direction towards the second anchor to reduce the volume of the lung further comprises pulling the first and second arms of the first anchor in the proximal direction towards the second anchor to reduce the volume of the lung.

14. The method of claim 1, wherein deploying the second anchor further comprises deploying first and second arms of the second anchor by selectively transitioning the first and second arms of the second anchor outwardly relative to the longitudinal axis such that the first and second arms of the second anchor engage the second region of the target site of the lung.

15. The method of claim 1, wherein deploying the first anchor further comprises deploying the first anchor by flexibly deforming the first anchor of the distal end outwardly relative to the longitudinal axis from a third position to a fourth position such that the first anchor engages the first region of the target site of the lung, wherein the fourth position is proximal to the third position.

16. The method of claim 1, wherein deploying the first anchor is performed prior to releasing the second anchor.

17. A method of delivering an implantable device into a target site of a lung of a patient, comprising the steps of:
(a) guiding a delivery device to the target site within the lung, and wherein a lumen of the delivery device contains an implantable device compressed within a distal end of the delivery device, the implantable device comprising:
(i) an elongated central body having a fixed axial length such that the elongated central body rigidly extends along a longitudinal axis;
(ii) a distal end including a distal expandable anchor; and
(iii) a proximal end including a proximal expandable anchor;
(b) releasing the distal end of the implantable device from the delivery device by selectively transitioning the distal expandable anchor outwardly relative to the longitudinal axis to expand the distal expandable anchor within the target site;
(c) pulling the implantable device proximally, wherein the pulling causes the distal expandable anchor to pull tissue at the target site proximally;
(d) selectively transitioning the proximal expandable anchor outwardly relative to the longitudinal axis to expand the proximal expandable anchor within the target site; and
(e) releasing the implantable device from the delivery device by severing an engagement feature, untying the engagement feature, or disconnecting magnets of the engagement feature.

18. The method of claim 17, wherein the distal expandable anchor is secured to a parenchyma of the lung or a distal bronchia wall of the lung.

19. A method of delivering an implantable device to a target site in a lung of a patient, the implantable device comprising:
(a) an elongated central body having a fixed axial length such that the elongated central body rigidly extends along a longitudinal axis;
(b) a first end including a first anchor; and
(c) a second end including a second anchor;
the method comprising the steps of:
(a) aligning the first anchor to the target site while the implantable device is at least partially placed within a deployment device;
(b) deploying the first anchor by flexibly deforming the first anchor outwardly relative to the longitudinal axis such that the first anchor engages a first region of the target site of the lung;
(c) pulling the first anchor in a proximal direction towards the second anchor to reduce the volume of the lung; and
(d) releasing the second anchor by flexibly deforming the second anchor outwardly relative to the longitudinal axis such that the second anchor engages a second region of the target site of the lung, wherein the first and second anchors include ball-like members on their respective ends that reduce trauma and allow for repositioning.

* * * * *